United States Patent [19]

Beaupre et al.

[11] Patent Number: 5,776,155

[45] Date of Patent: Jul. 7, 1998

[54] METHODS AND DEVICES FOR ATTACHING AND DETACHING TRANSMISSION COMPONENTS

[75] Inventors: Jean Beaupre, Cincinnati, Ohio; Gary Whipple, South Attleboro, Mass.

[73] Assignee: Ethicon Endo-Surgery, Inc., Cincinnati, Ohio

[21] Appl. No.: 777,934

[22] Filed: Dec. 23, 1996

[51] Int. Cl.$^6$ ............................................. A61N 7/00
[52] U.S. Cl. ................................... 606/169; 604/22
[58] Field of Search ............................ 606/169, 107, 606/166, 170, 171, 159; 604/22, 48

[56] References Cited

U.S. PATENT DOCUMENTS

| | | | |
|---|---|---|---|
| Re. 30,536 | 3/1981 | Perdreaux, Jr. | 433/86 |
| 2,874,470 | 2/1959 | Richards | 32/58 |
| 3,075,288 | 1/1963 | Balamuth et al. | 32/58 |
| 3,076,904 | 2/1963 | Kleesattel et al. | 310/26 |
| 3,213,537 | 10/1965 | Balamuth et al. | 32/28 |
| 3,368,280 | 2/1968 | Fridman et al. | 32/58 |
| 3,375,583 | 4/1968 | Blank et al. | 32/26 |
| 3,488,851 | 1/1970 | Haydu | 32/58 |
| 3,489,930 | 1/1970 | Shoh | 310/8.1 |
| 3,518,766 | 7/1970 | Burt | 32/58 |
| 3,526,036 | 9/1970 | Goof | 32/28 |
| 3,526,792 | 9/1970 | Shoh | 310/8.1 |
| 3,589,012 | 6/1971 | Richman | 32/58 |

(List continued on next page.)

FOREIGN PATENT DOCUMENTS

| | | |
|---|---|---|
| 1098003 | 9/1977 | Canada. |
| 0 495 634 A2 | 1/1992 | European Pat. Off.. |
| 0 495 634 A3 | 1/1992 | European Pat. Off.. |
| 0 624 346 A2 | 5/1994 | European Pat. Off.. |
| 0 624 346 A3 | 5/1994 | European Pat. Off.. |
| 29 22 239 | 5/1979 | Germany. |
| 37 07 921 A1 | 3/1987 | Germany. |
| 56-38931 | 5/1981 | Japan. |
| 56-108085 | 8/1981 | Japan. |
| 61-265136 | 4/1986 | Japan. |
| 2-99049 | 4/1990 | Japan. |

(List continued on next page.)

OTHER PUBLICATIONS

UltraCision Incorporated, The Harmonic Scalpel® For Gynecological Surgery, Product Sheet, Sep. 1992.
UltraCision Incorporated, The Harmonic Scalpel® For General Surgery, Product Sheet, Jan. 1993.
Snowden-Pencer, Inc., Endoscopic Plastic Surgery, 1993.
UltraCision Incorporated, Harmonic Scalpel® Price List, 1995.
UltraCision Incorporated, Harmonic Scalpel® Operating Manual, Mar. 1995.
Ethicon Endo-Surgery, Inc., Ultracision CS/LCS Layout Brochure, 1996.

(List continued on next page.)

*Primary Examiner*—Michael Buiz
*Assistant Examiner*—Kevin Troung
*Attorney, Agent, or Firm*—Rockey, Milnamow & Katz, Ltd.

[57] ABSTRACT

One surgical device includes a transducer assembly adapted to vibrate at an ultrasonic frequency in response to electrical energy. A first transmission component is adapted to receive and transmit the ultrasonic vibration from a first end to a second end. A second transmission component is adapted to receive and transmit the ultrasonic vibrations from a first end to a second end. A torque limiting device coupled to the second transmission component limits the torque when the second end of the first transmission rod is coupled to the first end and a method of attaching a transmission component is also provided. A method in accordance with the present invention includes the steps of providing a handpiece assembly having an integral torque limiting mechanism and a first transmission component and threading a second transmission component onto the first transmission component of the handpiece assembly. The method also includes the steps of rotating a sleeve of the handpiece assembly until the second transmission component has been tightened to a predetermined torque on the first transmission component of the handpiece assembly.

11 Claims, 7 Drawing Sheets

U.S. PATENT DOCUMENTS

| | | | |
|---|---|---|---|
| 3,589,363 | 6/1971 | Banko et al. | 128/276 |
| 3,593,425 | 7/1971 | Robinson | 32/58 |
| 3,636,947 | 1/1972 | Balamuth | 128/66 |
| 3,645,255 | 2/1972 | Robinson | 128/24 A |
| 3,654,502 | 4/1972 | Carmona et al. | 310/26 |
| 3,654,540 | 4/1972 | Honig et al. | 318/118 |
| 3,703,037 | 11/1972 | Robinson | 32/58 |
| 3,809,977 | 5/1974 | Babamuth et al. | 318/116 |
| 3,930,173 | 12/1975 | Banko | 310/26 |
| 3,956,826 | 5/1976 | Perdreaux, Jr. | 32/58 |
| 4,156,157 | 5/1979 | Mabille | 310/316 |
| 4,175,242 | 11/1979 | Kleinschmidt | 310/316 |
| 4,188,952 | 2/1980 | Loschilov et al. | 128/305 |
| 4,227,110 | 10/1980 | Douglas et al. | 310/316 |
| 4,370,131 | 1/1983 | Banko | 433/86 |
| 4,371,816 | 2/1983 | Wieser | 318/116 |
| 4,406,284 | 9/1983 | Banko | 128/303 |
| 4,491,132 | 1/1985 | Aikins | 128/305 |
| 4,492,574 | 1/1985 | Warrin et al. | 433/81 |
| 4,750,488 | 6/1988 | Wuchinich et al. | 128/303 |
| 4,808,153 | 2/1989 | Parisi | 604/22 |
| 4,816,018 | 3/1989 | Parisi | 604/22 |
| 4,820,152 | 4/1989 | Warrin et al. | 433/86 |
| 4,867,141 | 9/1989 | Nakada et al. | 128/24 |
| 4,870,953 | 10/1989 | DonMichael et al. | 128/24 |
| 4,897,079 | 1/1990 | Zaleski et al. | 604/22 |
| 4,920,954 | 5/1990 | Alliger et al. | 128/24 |
| 4,922,902 | 5/1990 | Wuchinich et al. | 604/22 |
| 4,931,047 | 6/1990 | Broadwin et al. | 604/22 |
| 4,936,281 | 6/1990 | Stasz | 128/660.03 |
| 4,974,590 | 12/1990 | Saito | 128/662.06 |
| 4,979,952 | 12/1990 | Kubota et al. | 606/169 |
| 5,011,471 | 4/1991 | Miyazaki et al. | 604/22 |
| 5,026,387 | 6/1991 | Thomas | 606/169 |
| 5,047,043 | 9/1991 | Kubota et al. | 606/169 |
| 5,057,119 | 10/1991 | Clark et al. | 606/169 |
| 5,059,210 | 10/1991 | Clark et al. | 606/169 |
| 5,069,664 | 12/1991 | Guess et al. | 604/22 |
| 5,112,300 | 5/1992 | Ureche | 604/22 |
| 5,123,903 | 6/1992 | Quaid et al. | 604/22 |
| 5,151,084 | 9/1992 | Khek | 604/22 |
| 5,151,085 | 9/1992 | Sakurai et al. | 604/22 |
| 5,160,317 | 11/1992 | Costin | 604/22 |
| 5,167,725 | 12/1992 | Clark et al. | 428/680 |
| 5,180,363 | 1/1993 | Idemoto et al. | 202/32 |
| 5,190,517 | 3/1993 | Zieve et al. | 604/22 |
| 5,248,296 | 9/1993 | Alliger | 609/22 |
| 5,263,957 | 11/1993 | Davison | 606/169 |
| 5,269,309 | 12/1993 | Fort et al. | 128/661.01 |
| 5,322,055 | 6/1994 | Davison et al. | 601/2 |
| 5,324,299 | 6/1994 | Davison et al. | 606/167 |
| 5,342,292 | 8/1994 | Nita et al. | 604/22 |
| 5,344,420 | 9/1994 | Hilal et al. | 606/28 |
| 5,346,502 | 9/1994 | Estabrook et al. | 606/169 |
| 5,380,274 | 1/1995 | Nita | 604/22 |
| 5,382,162 | 1/1995 | Sharp | 433/116 |
| 5,397,269 | 3/1995 | Beaty et al. | 464/38 |
| 5,413,107 | 5/1995 | Oakley et al. | 128/662.06 |
| 5,417,672 | 5/1995 | Nita et al. | 604/283 |
| 5,425,704 | 6/1995 | Sakurai et al. | 604/22 |
| 5,438,554 | 8/1995 | Seyed-Bolorforosh et al. | 367/140 |
| 5,449,370 | 9/1995 | Vaitekunas | 606/169 |
| 5,472,447 | 12/1995 | Abrams et al. | 606/169 |
| 5,496,342 | 3/1996 | Urich | 606/169 |
| 5,507,738 | 4/1996 | Ciervo | 606/1 |
| 5,507,743 | 4/1996 | Edwards et al. | 606/41 |
| 5,509,916 | 4/1996 | Taylor | 606/13 |
| 5,526,815 | 6/1996 | Granz et al. | 128/660.03 |
| 5,540,656 | 7/1996 | Pflueger et al. | 604/22 |
| 5,542,917 | 8/1996 | Nita et al. | 604/22 |
| 5,546,947 | 8/1996 | Yagami et al. | 128/662.06 |
| 5,562,609 | 10/1996 | Brumbach | 604/22 |
| 5,562,610 | 10/1996 | Brumbach | 604/22 |
| 5,582,588 | 12/1996 | Sakurai et al. | 604/22 |
| 5,606,974 | 3/1997 | Castellano et al. | 128/662.06 |
| 5,628,743 | 5/1997 | Cimino | 606/1 |
| 5,634,912 | 6/1997 | Onjev | 604/22 |

FOREIGN PATENT DOCUMENTS

| | | |
|---|---|---|
| 1388002 A1 | 4/1988 | U.S.S.R. |
| WO 91/13591 | 3/1991 | WIPO |
| WO 92/02658 | 7/1991 | WIPO |
| WO 92/14514 | 2/1992 | WIPO |
| WO 93/14708 | 1/1993 | WIPO |
| WO 93/16646 | 1/1993 | WIPO |
| WO 96/29935 | 4/1996 | WIPO |
| WP 96/34561 | 5/1996 | WIPO |

OTHER PUBLICATIONS

Cooper LaserSonics, Inc., Ultrasonic Surgical Aspirator NS-100 Operator Manual, 1984, pp. 12, 13, 16, 17, and 29-33.

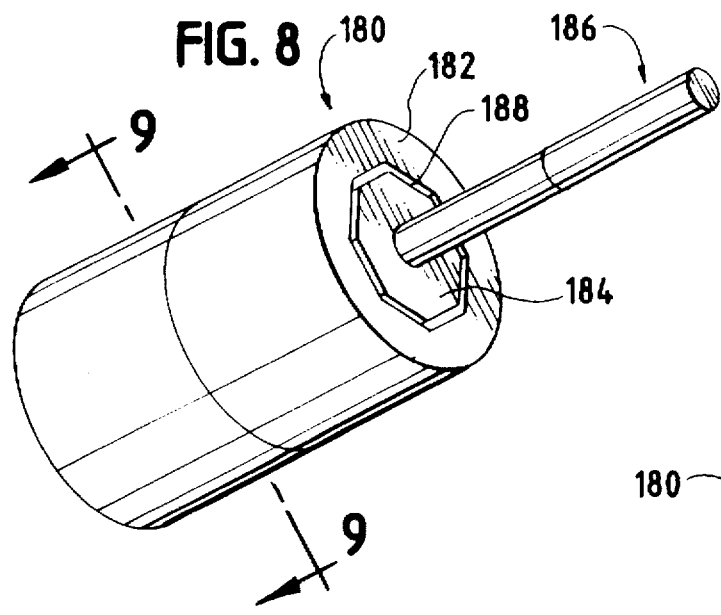
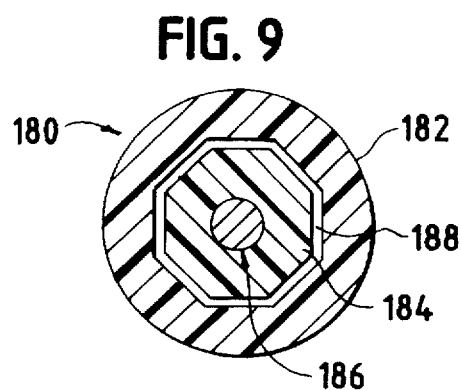
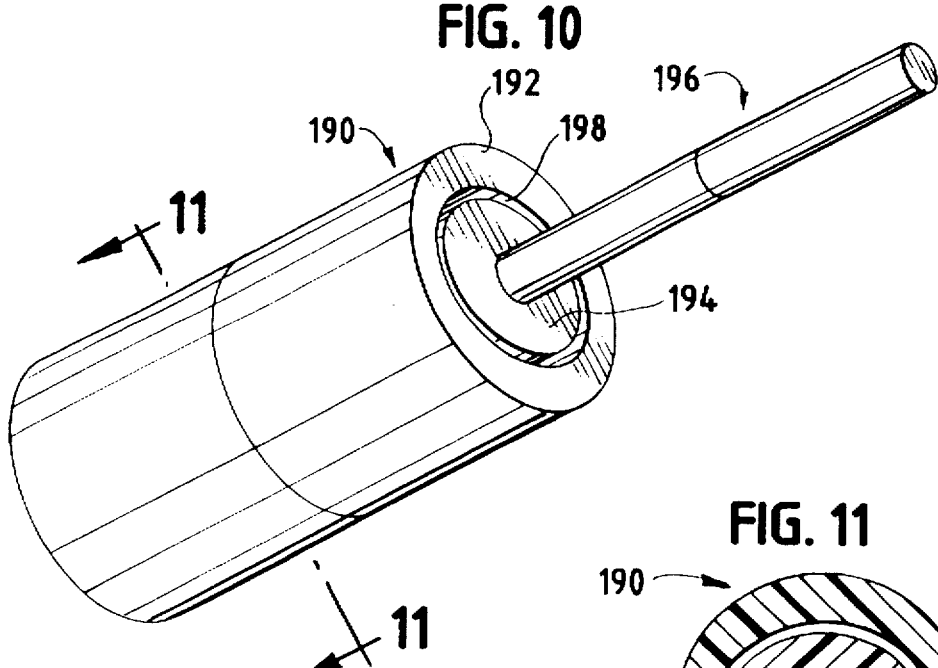
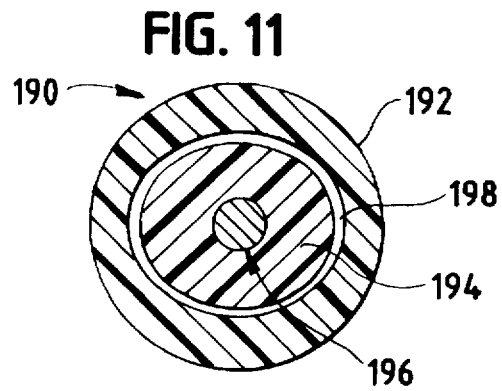

METHODS AND DEVICES FOR ATTACHING AND DETACHING TRANSMISSION COMPONENTS

FIELD OF THE INVENTION

The present invention generally relates to facilitating the attachment and detachment of a first ultrasonic transmission component to a second ultrasonic transmission component. More particularly, it relates to methods and devices for limiting the amount of torque that may be applied when attaching a first ultrasonic transmission component to a second ultrasonic transmission component.

BACKGROUND OF THE INVENTION

Ultrasonic transmission devices are well known for use in a variety of applications, such as surgical operations and procedures. These transmission devices usually include a transducer that converts electrical energy into vibrational motion at ultrasonic frequencies. The vibrational motion is usually transmitted through a mounting device to vibrate a distal end of a transmission component, such as a working member.

The working member is typically attached to the mounting device by a screw-type mechanism to form a junction. The junction between the working member and the mounting device usually requires a sufficient axial compression force to reduce mechanical losses, to obtain consistent performance of the device, to minimize transverse vibrations, and to prevent the working member and mounting device from separating during operation.

The working member is usually tightened to the mounting device by using a tool, such a wrench. However, the use of a wrench may cause the working member to be inadvertently over-tightened, which may tend to damage the working member and/or the mounting device. When the working member is over-tightened, the working member may be difficult to detach from the mounting device. On the other hand, insufficient tightening of the working member to the mounting device may cause undesired heat build-up at the junction, decrease the transfer of energy across the junction, and cause undesired traverse motion.

A separate torque limiting device may also be used to tighten a working member to a mounting device. The torque limiting device is used to assure that a predetermined minimum torque is reached and that a maximum torque is not exceeded when tightening the working member to the mounting device. In one known technique, a separate torque wrench W as illustrated in FIG. 1 may be placed over a working member WM to tighten and untighten the working member WM from a mounting device M of a handpiece assembly H of an ultrasonic device. In this technique, the working member WM is attached to the mounting device M by a threaded connection. Once the working member WM is threaded onto the mounting device M, the torque wrench W is then slipped over the working member WM to tighten the working member WM to the mounting device M. The nose cone N may then be threaded onto the distal end of the handpiece assembly H.

However, it can be quite difficult for a user to connect and disconnect the working member from the mounting device in a sterile field when using a separate torque wrench. Further, it can be cumbersome and time consuming to use a separate torque wrench when changing the working member during an operation or when tightening certain working members to the mounting device. Additionally, the torque wrench can be mislaid or lost and may require calibration or replacement at frequent intervals to ensure accuracy.

Other prior art devices have been developed to tighten a working member to a mounting device of a handpiece assembly. For example, U.S. Pat. Nos. 5,059,210 and 5,057,119, which are hereby incorporated by reference, disclose a separate torque wrench for attaching and detaching a blade/coupler to a transformer or mounting device of a handpiece assembly.

Accordingly, there is a need for improved devices and methods to attach and detach a first transmission component to a second transmission component. Such devices would further benefit if the transmission components could be readily attached and detached without the use of a separate torque limiting tool.

SUMMARY OF THE INVENTION

In view of the above, the present invention relates to methods and devices for facilitating attachment and detachment of transmission components. In general, a first transmission component can be quickly coupled to and disengaged from a second transmission component without the use of a separate tool. The first transmission component may be removed from the second transmission component for disposal or to permit sterilization so that it may be reused.

The devices in accordance with the present invention are configured to limit the amount of torque applied when the first transmission component is attached to the second transmission component. An integral torque mechanism limits the application of torque when tightening the transmission components. The torque mechanism may be built into the a handpiece assembly of the surgical device or into a sleeve or adapter of a surgical instrument.

A surgical device in accordance with the present invention includes a transducer assembly adapted to vibrate at an ultrasonic frequency in response to electrical energy. A first transmission component is adapted to receive ultrasonic vibration from the transducer assembly and transmit the ultrasonic vibration from a first end to a second end of the first transmission component. The first end of the first transmission component is coupled to the transducer assembly. A second transmission component is adapted to receive the ultrasonic vibration from the first transmission component and transmit the ultrasonic vibration from a first end to a second end of the second transmission component. A torque limiting device integrally coupled to one of the first and second transmission components to limit the torque when the second end of the first transmission rod is coupled to the first end of the second transmission component.

Another surgical instrument in accordance with the present invention includes an adapter having an inner member having a predetermined configuration carried by the adapter. The inner member including an outer surface having a complementary configuration adapted to engage the inner surface of the adapter. A working member extends from the inner member and is adapted to contact tissue of a patient. The adapter is rotatable to rotate the inner member to a predetermined torque.

A method embodying the principles of the invention includes the steps of providing a handpiece assembly having an integral torque limiting mechanism and a first transmission component, and threading a second transmission component onto the first transmission component of the handpiece assembly. The method also includes the steps of rotating a sleeve of the handpiece assembly until the second transmission component has been tightened to a predetermined torque on the first transmission component of the handpiece assembly.

Another method in accordance with the present invention includes the steps of providing a surgical instrument having an integral torque limiting mechanism and a first transmission component, and threading a second transmission component to the first transmission component. The method also includes the steps of rotating an adapter of the surgical instrument until the second transmission component has been tightened to a predetermined torque on the first transmission component of the handpiece assembly.

It is to be understood that both the foregoing general description and the following detailed description are exemplary and explanatory and are intended to provide further explanation of the invention as claimed.

The invention, together with attendant advantages, will best be understood by reference to the following detailed description of the preferred embodiments of the invention, taken in conjunction with the accompanying drawings.

BRIEF DESCRIPTION OF THE DRAWINGS

FIG. 8 is a perspective view of an alternative embodiment of a surgical instrument in accordance with the present invention;

FIG. 9 is a cross-sectional view about line 9—9 of the surgical instrument of FIG. 8;

FIG. 10 is a perspective view of an alternative embodiment of a surgical instrument in accordance with the present invention;

FIG. 11 is a cross-sectional view about line 11—11 of the surgical instrument of FIG. 10;

DESCRIPTION OF THE PREFERRED EMBODIMENTS

Before explaining the present invention in detail, it should be noted that the invention is not limited in its application or use to the details of construction and arrangement of parts illustrated in the accompanying drawings and description, because the illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

Figure 1:
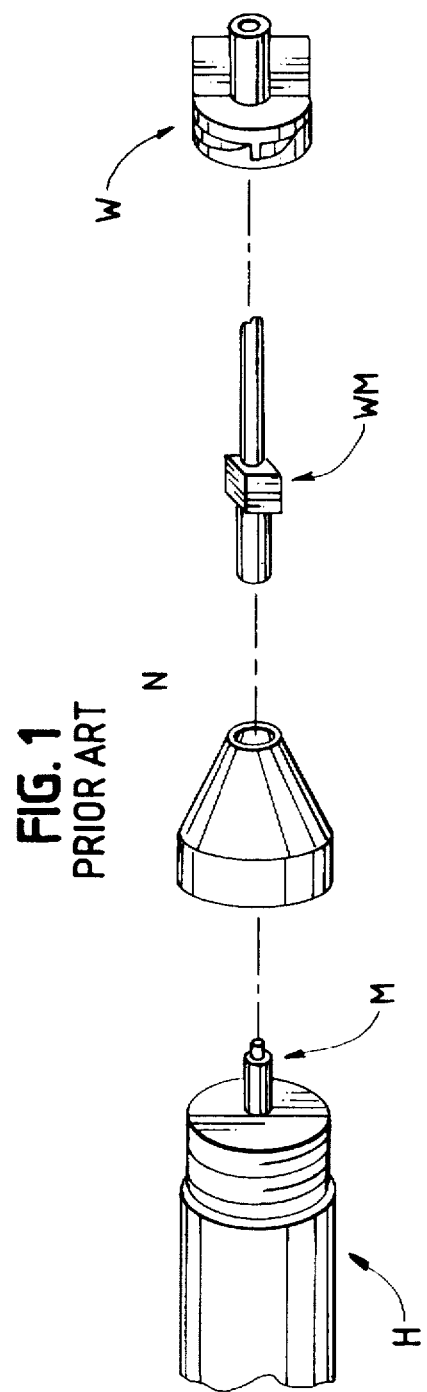
FIG. 1 is an exploded, fragmentary perspective view of a prior art handpiece assembly of an ultrasonic device.

Referring now to the drawings in detail, FIG. 1 shows an exploded, fragmentary perspective view of a prior art handpiece assembly H of an ultrasonic device. The working member WM is threaded onto the mounting device M of the handpiece assembly H. A separate torque wrench W is slipped over the working member WM to tighten the working member WM to a desired torque to the mounting device M.

Figure 2:
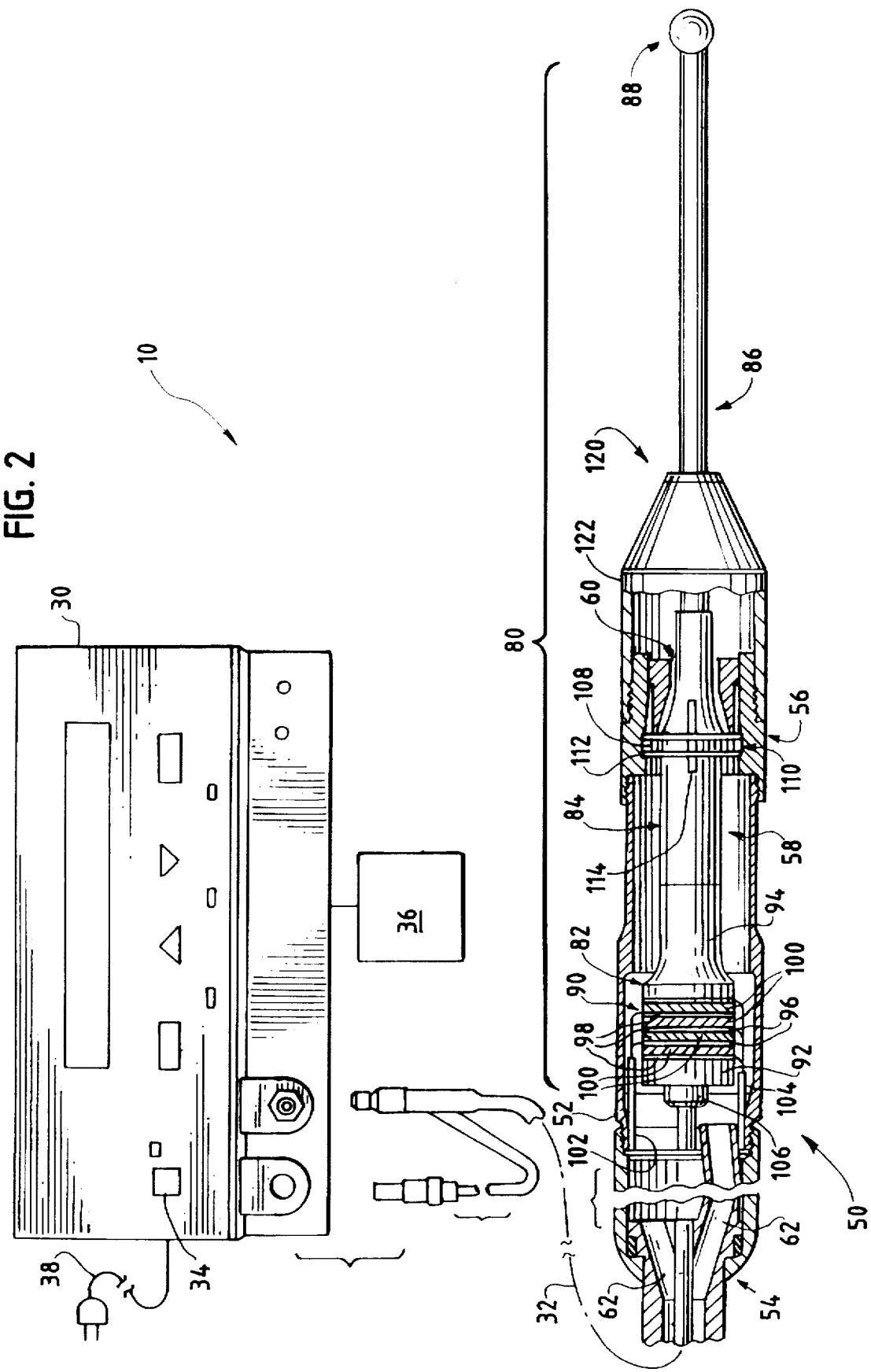
FIG. 2 is a cutaway view and in partial cross-section of an embodiment of a surgical system in accordance with the present invention.

Referring now to FIG. 2, a presently preferred embodiment of a surgical system 10 is illustrated. The surgical system 10 generally includes a generator 30, a handpiece assembly 50, an acoustic or transmission assembly 80, and a surgical tool or instrument 120. The generator 30 sends an electrical signal through a cable 32 at a selected amplitude, frequency, and phase determined by a control system of the generator 30. As will be further described, the signal causes one or more piezoelectric elements of the acoustic assembly 80 to expand and contract, thereby converting the electrical energy into mechanical motion. The mechanical motion results in longitudinal waves of ultrasonic energy that propagate through the acoustic assembly 80 in an acoustic standing wave to vibrate the acoustic assembly 80 at a selected frequency and amplitude. An end effector 88 at the distal end of the acoustic assembly 80 is placed in contact with tissue of the patient to transfer the ultrasonic energy to the tissue. The cells of the tissue in contact with the end effector 88 of the acoustic assembly 80 will move with the end effector 88 and vibrate.

As the end effector 88 couples with the tissue, thermal energy or heat is generated as a result of internal cellular friction within the tissue. The heat is sufficient to break protein hydrogen bonds, causing the highly structured protein (i.e., collagen and muscle protein) to denature (i.e., become less organized). As the proteins are denatured, a sticky coagulum forms to seal or coagulate small blood vessels when the coagulum is below 100° C. Deep coagulation of larger blood vessels results when the effect is prolonged.

The transfer of the ultrasonic energy to the tissue causes other effects including mechanical tearing, cutting, cavitation cell disruption, and emulsification. The amount of cutting as well as the degree of coagulation obtained varies with the vibrational amplitude of the end effector 88, the amount of pressure applied by the user, and the sharpness of the end effector 88. The end effector 88 of the acoustic assembly 80 in the surgical system 10 tends to focus the vibrational energy of the system 10 onto tissue in contact with the end effector 88, intensifying and localizing thermal and mechanical energy delivery.

As illustrated in FIG. 2, the generator 30 includes a control system integral to the generator 30, a power switch 34, and a triggering mechanism 36. The power switch 34 controls the electrical power to the generator 30, and when activated by the triggering mechanism 36, the generator 30 provides energy to drive the acoustic assembly 80 of the surgical system 10 at a predetermined frequency and to drive the end effector 88 at a predetermined vibrational amplitude level. The generator 30 may drive or excite the acoustic assembly 80 at any suitable resonant frequency of the acoustic assembly 80.

When the generator 30 is activated via the triggering mechanism 36, electrical energy is continuously applied by the generator 30 to a transducer assembly 82 of the acoustic assembly 80. A phase lock loop in the control system of the generator 30 monitors feedback from the acoustic assembly 80. The phase lock loop adjusts the frequency of the electrical energy sent by the generator 30 to match a preselected harmonic frequency of the acoustic assembly 80. In addition, a second feedback loop in the control system maintains the electrical current supplied to the acoustic assembly 80 at a preselected constant level in order to achieve substantially constant vibrational amplitude at the end effector 88 of the acoustic assembly 80. The electrical signal supplied to the acoustic assembly 80 will cause the distal end to vibrate longitudinally in the range of, for example, approximately 20 kHz to 100 kHz, and preferably in the range of about 54 kHz to 56 kHz, and most preferably at about 55.5 kHz. The amplitude of the acoustic vibrations at the end effector 88 may be controlled by, for example, controlling the amplitude of the electrical signal applied to the transduction portion 90 of the acoustic assembly 80 by the generator 30.

As noted above, the triggering mechanism 36 of the generator 30 allows a user to activate the generator 30 so that electrical energy may be continuously supplied to the acoustic assembly 80. In one embodiment, the triggering mechanism 36 preferably comprises a foot activating switch that is detachably coupled or attached to the generator 30 by a cable or cord. In another embodiment, a hand switch may be incorporated in the handpiece assembly 50 to allow the generator 30 to be activated by a user.

The generator 30 also has a power line 38 for insertion in an electrosurgical unit or conventional electrical outlet. It is contemplated that the generator 30 may also be powered by a direct current (DC) source, such as a battery. The generator 30 may be any suitable generator, such as Model No. GEN01, available from Ethicon Endo-Surgery, Inc.

Referring still to FIG. 2, the handpiece assembly 50 includes a multi-piece housing or outer casing 52 adapted to isolate the operator from the vibrations of the acoustic assembly 80. The housing 52 is preferably cylindrically shaped and is adapted to be held by a user in a conventional manner, but may be any suitable shape and size which allows it to be grasped by the user. While a multi-piece housing 52 is illustrated, the housing 52 may comprise a single or unitary component.

The housing 52 of the handpiece assembly 50 is preferably constructed from a durable plastic, such as Ultem®. It is also contemplated that the housing 52 may be made from a variety of materials including other plastics (i.e., liquid crystal polymer (LCP), nylon, or polycarbonate). A suitable handpiece assembly 50 is Model No. HP050, available from Ethicon Endo-Surgery, Inc.

Referring still to FIG. 2, the handpiece assembly 50 generally includes a proximal end 54, a distal end 56, and centrally disposed axial opening or cavity 58 extending longitudinally therein. The distal end 56 of the handpiece assembly 50 includes an opening 60 configured to allow the acoustic assembly 80 of the surgical system 10 to extend therethrough, and the proximal end 54 of the handpiece assembly 50 is coupled to the generator 30 by a cable 32.

The cable 32 may include ducts or vents 62 to allow air to be introduced into the handpiece assembly 50 to cool the transducer assembly 82 of the acoustic assembly 80.

The surgical instrument 120 of the surgical system 10 generally includes a sleeve or adapter 122 and an integral torque limiting device, as further described below, to limit the torque when an ultrasonic transmission component or rod 86 of the surgical instrument 120 is attached to an ultrasonic transmission component (i.e., a mounting device 84) of the handpiece assembly 50. The proximal end of the adapter 122 of the surgical instrument 120 preferably fits over the distal end 56 of the handpiece assembly 50. The adapter 122 of the surgical instrument 120 may be cylindrically shaped and has an opening near its distal end to allow the transmission component 86 to extend therethrough. The adapter 122 may be fabricated from Ultem®. It is contemplated that the adapter 122 may be made from any suitable material without departing from the spirit and scope of the invention.

Referring still to FIG. 2, the acoustic assembly 80 of the surgical system 10 generally includes a transducer stack or assembly 82, a mounting device 84, a working member or a transmission rod 86 integrally attached to an end effector 88. The transducer assembly 82, mounting device 84, transmission rod 86, and the end effector 88 may be acoustically tuned such that the length of each component is an integral number of one-half system wavelengths (n$\lambda$/2) where the system wavelength $\lambda$ is the wavelength of a preselected or operating longitudinal vibration frequency f of the acoustic assembly 80. It is also contemplated that the acoustic assembly 80 may be any suitable arrangement of acoustic elements. For example, the acoustic assembly 80 may comprise a transducer assembly and an end effector (i.e., the acoustic assembly 80 may be configured without a mounting device and a transmission rod).

The transducer assembly 82 of the acoustic assembly 80 converts the electrical signal from the generator 30 into mechanical energy that results in longitudinal vibratory motion of the end effector 88 at ultrasonic frequencies. When the acoustic assembly 80 is energized, a vibratory motion standing wave is generated through the acoustic assembly 80. The amplitude of the vibratory motion at any point along the acoustic assembly 80 depends on the location along the acoustic assembly 80 at which the vibratory motion is measured. A minimum or zero crossing in the vibratory motion standing wave is generally referred to as a node (i.e., where axial motion is usually minimal and radial motion is usually small), and an absolute value maximum or peak in the standing wave is generally referred to as an antinode. The distance between an antinode and its nearest node is one-quarter wavelength ($\lambda$/4).

As shown in FIG. 2, the transducer assembly 82 of the acoustic assembly 80, which is known as a "Langevin stack", generally includes a transduction portion 90, a first resonator 92, and a second resonator 94. The transducer assembly 82 may be an integral number of one-half system wavelengths (n$\lambda$/2) in length. It is to be understood that the present invention may be alternatively configured to include a transducer assembly comprising a magnetostrictive, electromagnetic or electrostatic transducer.

The distal end the first resonator 92 is connected to the proximal end of the transduction section 90, and the proximal end of the second resonator 94 is connected to the distal end of the transduction portion 90. The first and second resonators 92 and 94 are preferably fabricated from titanium, aluminum, steel, or any other suitable material. The first and second resonators 92 and 94 have a length determined by a number of variables, including the thickness of the transduction section 90, the density and modulus of elasticity of material used in the resonators 92 and 94, and the fundamental frequency of the transducer assembly 82. The second resonator 94 may be tapered inwardly from its proximal end to its distal end to amplify the ultrasonic vibration amplitude.

The transduction portion 90 of the transducer assembly 82 preferably comprises a piezoelectric section of alternating positive electrodes 96 and negative electrodes 98, with piezoelectric elements 100 alternating between the electrodes 96 and 98. The piezoelectric elements 100 may be fabricated from any suitable material, such as lead-zirconate-titanate, lead meta-niobate, lead titanate, or other ceramic piezoelectric crystal material. Each of the positive electrodes 96, negative electrodes 98, and piezoelectric elements 100 may have a bore extending through the center. The positive and negative electrodes 96 and 98 are electrically coupled to wires 102 and 104, respectively. The wires 102 and 104 transmit the electrical signal from the generator 30 to the electrodes 96 and 98.

As shown in FIG. 2, the piezoelectric elements 100 are held in compression between the first and second resonators 92 and 94 by a bolt 106. The bolt 106 preferably has a head, a shank, and a threaded distal end. The bolt 106 is inserted from the proximal end of the first resonator 92 through the bores of the first resonator 92, the electrodes 96 and 98, and piezoelectric elements 100. The threaded distal end of the bolt 106 is screwed into a threaded bore in the proximal end of second resonator 94.

The piezoelectric elements 100 are energized in response to the electrical signal supplied from the generator 30 to produce an acoustic standing wave in the acoustic assembly 80. The electrical signal causes disturbances in the piezoelectric elements 100 in the form of repeated small displacements resulting in large compression forces within the material. The repeated small displacements cause the piezoelectric elements 100 to expand and contract in a continuous manner along the axis of the voltage gradient, producing high frequency longitudinal waves of ultrasonic energy. The ultrasonic energy is transmitted through the acoustic assembly 80 to the end effector 88.

The mounting device 84 of the acoustic assembly 80 has a proximal end, a distal end, and may have a length substantially equal to an integral number of one-half system wavelengths. The proximal end of the mounting device 84 is preferably axially aligned and coupled to the distal end of the second resonator 94 by an internal threaded connection near an anti-node. (For purposes of this application, the term "near" is defined as "exactly at" or "in close proximity to".) It is also contemplated that the mounting device 84 may be attached to the second resonator 94 by any suitable means, and that the second resonator 94 and mounting device 84 may be formed as a single or unitary component.

As illustrated in FIG. 2, the mounting device 84 is coupled to the housing 52 of the handpiece assembly 50 near a node. The mounting device 84 may also include an integral ring 108 disposed around its periphery. The integral ring 108 is preferably disposed in an annular groove 110 formed in the housing 52 of the handpiece assembly 50 to couple the mounting device 84 to the housing 58. A compliant member or material 112, such, for example, as a pair of silicone 0-rings attached by stand-offs, may be placed between the annular groove 110 of the housing 52 and the integral ring 108 of the mounting device 84 to reduce or prevent ultrasonic vibration from being transmitted from the mounting device 84 to the housing 52.

The mounting device 84 may be secured in a predetermined axial position by a plurality of pins 114, preferably four. The pins 114 are disposed in a longitudinal direction ninety (90) degrees apart from each other around the outer periphery of the mounting device 84. The pins 114 are coupled to the housing 52 of the handpiece assembly 50 and are disposed through notches in the integral ring 108 of the mounting device 84. The pins 114 are preferably fabricated from stainless steel.

The mounting device 84 may be configured to amplify the ultrasonic vibration amplitude that is transmitted through the acoustic assembly 80 to the distal end of the end effector 88. In one embodiment, the mounting device 84 may comprise a solid, tapered horn. As ultrasonic energy is transmitted through the mounting device 84, the velocity of the acoustic wave transmitted through the mounting device 84 is amplified. It is contemplated that the mounting device 84 may be any suitable shape, such as a stepped horn, a conical horn, an exponential horn, or the like.

The distal end of the mounting device 84 is coupled to the proximal end of the transmission rod 86. It is contemplated that the transmission rod 86 be attached to the mounting device 84 by any suitable means, such as, for example, an internal threaded connection. The mounting device 84 may be coupled to the transmission rod 86 near an antinode.

The transmission rod 86 may have a length substantially equal to an integer number of one-half system wavelengths (nλ/2). The transmission rod 86 may be fabricated from a solid core shaft constructed out of material which propagates ultrasonic energy efficiently, such as titanium alloy (i.e., Ti-6Al-4V) or an aluminum alloy. It is contemplated that the transmission rod 86 may be fabricated from any suitable material. The transmission rod 86 may have polymeric material that surrounds the transmission rod 86 to isolate it from outside contact and may amplify the mechanical vibrations transmitted through the transmission rod 86 to be end effector 88 as is well known in the art.

The distal end of the transmission rod 86 is integrally formed to the proximal end of the end effector 88. It is also contemplated that the end effector 88 may be detachable from the transmission rod 86 by an internal threaded connection near an antinode.

As shown in FIG. 2, the end effector 88 has a ball-shaped member at its distal end. It is also contemplated that the end effector 88 may have a distal region having a smaller cross-section area than a proximal region thereof, thereby forming a vibrational amplitude step-up junction. The step-up junction acts as velocity transformer as known in the art, increasing the magnitude of the ultrasonic vibration transmitted from the proximal region to the distal region of the end effector 88.

The end effector 88 may have a length substantially equal to an integral multiple of one-half system wavelengths (nλ/2). The distal end of the end effector 88 is disposed near an antinode in order to produce the maximum longitudinal deflection at the distal end. When the transducer assembly 82 is energized, the distal end of the end effector 88 is configured to move longitudinally in the range of, for example, approximately 10 to 500 microns peak-to-peak, and preferably in the range of about 30 to 100 microns at a predetermined vibrational frequency, and most preferably at about 90 microns.

The end effector 88 may be made from a solid core shaft constructed of material which propagates ultrasonic energy, such as a titanium alloy (i.e., Ti-6Al-4V) or an aluminum alloy. It is contemplated the end effector 88 may be fabricated from any suitable material. It will also be recognized that the end effector 88 may have a surface treatment to improve the delivery of energy and desired tissue effect. For example, the end effector 88 may be micro-finished, coated, plated, etched, grit-blasted, roughened or scored to enhance coagulation in tissue. Additionally, the end effector 88 may be sharpened or shaped to enhance its energy transmission characteristics. For example, the end effector 88 may be blade shaped, hook shaped, or ball shaped.

Figure 3:
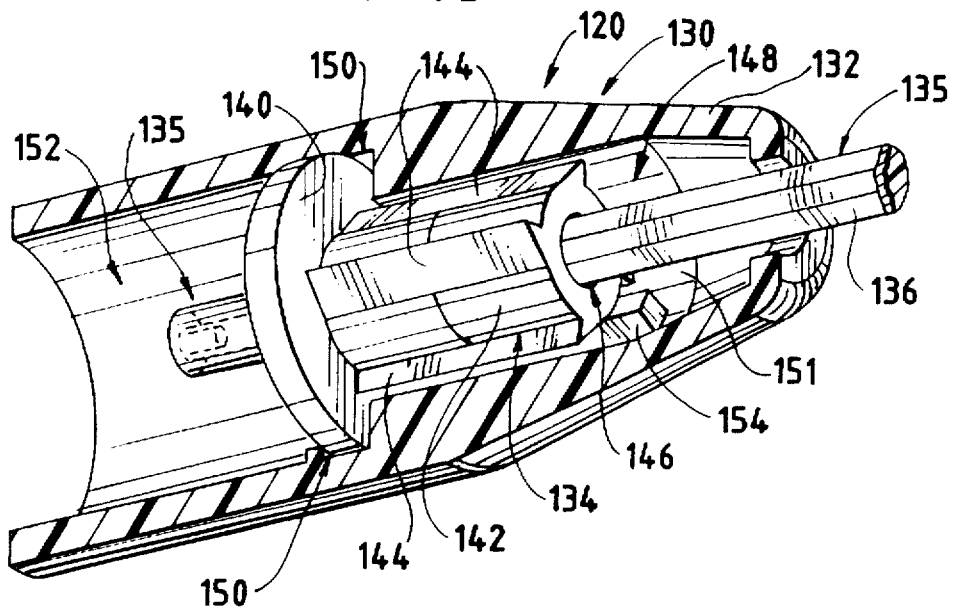
FIG. 3 is a cutaway view of a partial cross-section of one embodiment of a surgical instrument of the surgical system of FIG. 2.

Referring now to FIG. 3, a cutaway view of an embodiment of the surgical instrument 120 of the surgical system 10 is shown. The surgical instrument 120 includes an integrated torque limiting mechanism 130 which allows a first transmission rod to be tightened to predetermined torque to a second transmission component, such as, for example, a mounting device of a handpiece assembly. The torque limiting device 130 also prevents the first transmission rod from being over-tightened to the second transmission component.

The surgical instrument 120 preferably includes an adapter or sleeve 132, a collar 134, and a working member or transmission rod 135 integrally coupled to an effector. The transmission rod 135 preferably includes a waveguide or shaft 136, and the end effector (not shown) is integrally attached to the distal end of the transmission rod 135. It is contemplated that the end effector may be any suitable shape, and the end effector may be removable from the transmission rod 135 without departing from the spirit and scope of the invention.

When the transmission rod 135 of the surgical instrument 120 is attached to a transmission component (i.e., mounting device) of the handpiece assembly as shown in FIG. 2, the junction between the transmission rod 135 and the mounting device produces a relatively high axial compression force that is substantially uniformly distributed symmetrically about the longitudinal axis of the threaded connection of the mounting device and transmission rod 135 to efficiently transfer mechanical or ultrasonic vibrations across the junction. As a result, the ultrasonic vibrational motion may travel along the longitudinal axis of the joined components with minimal losses and minimal conversion of longitudinal energy into transverse vibrations.

Referring still to FIG. 3, the collar 134 of the surgical instrument 120 is preferably disposed or housed in the adapter 132. The collar 134 may be fabricated from a liquid crystal polymer (LCP). It is contemplated that the collar 134 may be fabricated from any suitable material.

The collar 134 generally includes a head 140 and a tubular member 142. The tubular member 142 preferably has four pawl-like or engageable members 144 spaced about 360° at 90° intervals. Preferably, the pawl-like members 144 are disposed on the collar 134 parallel to the axis of the transmission rod 135 and have a height that extends radially outwardly. It will be recognized that the pawl-like members 144 may be disposed on any suitable part of the collar 134 without departing from the scope and spirit of the present invention. It is also contemplated that the collar 134 may have any suitable number of pawl-like members (i.e. as few as one and more than four).

The collar 134 of the surgical instrument 120 includes an axial bore 146 to allow the transmission rod 135 to extend therethrough. The transmission rod 135 is secured in the axial bore 146 of the collar 134 so that when the collar 134 is rotated, the transmission rod 135 is also rotated. The transmission rod 135 may be attached to the collar 134 near a node.

The adapter 132 of the surgical instrument 120 is preferably fabricated from liquid crystal polymer (LCP). The adapter 132 may also be made from a variety of materials including other plastics, such as a polyetherimide, nylon or polycarbonate. The adapter 132 generally includes an axially extending chamber 148, an annular channel or groove 150, and a hollow region 152 configured to receive a handpiece assembly. The hollow region 152 of the adapter 132 is configured to be disposed over the distal end of the handpiece assembly, and the channel 150 is configured to maintain the head 140 of the collar 134 in a fixed axial position within the adapter 132.

Figure 4:
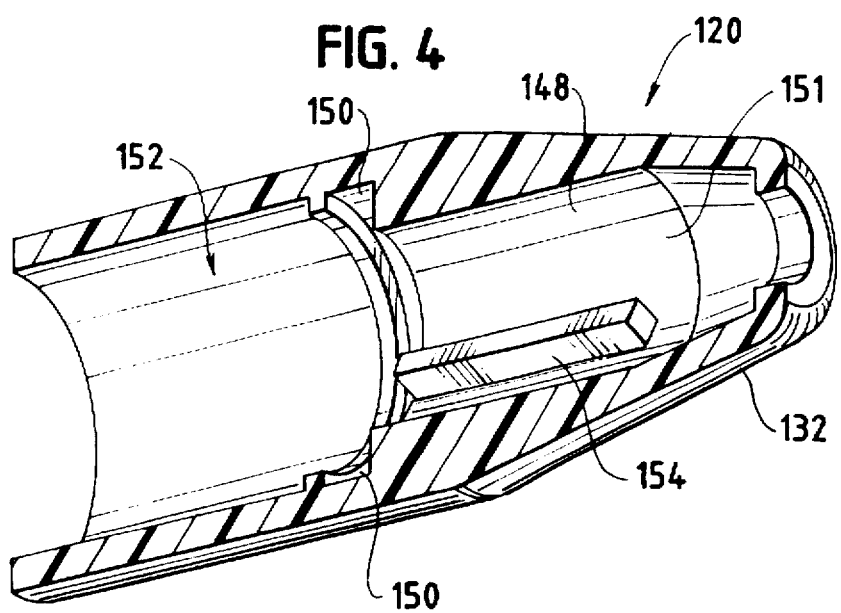
FIG. 4 is a cutaway view of the surgical instrument of FIG. 3 with a collar and transmission component removed.

The adapter 132 further includes one or more teeth-like members or engaging members 154 as further shown in FIG. 4. The teeth-like members 154 are configured for respective torque limiting engagement with the pawl-like members 144 of the collar 134. It will be recognized that the teeth-like members 154 are disposed on the inner wall 151 of the chamber 148 parallel to the axis of the transmission rod 135 and have a height that extends radially inwardly. The teeth-like members 154 of the adapter 132 may be disposed on any suitable part of the adapter 132 for torque-limiting engagement with pawl-like members 144 without departing from the spirit and scope of the invention. Preferably, the adapter 132 has two teeth-like members 154 spaced about 360° at 180° intervals. It is contemplated that the adapter 132 may have any number of engageable members (i.e. as few as one and more than four).

The teeth-like members 154 of the adapter 132 are preferably adapted to respectively engage the pawl-like members 144 of the collar 134 upon rotation of the adapter 132 to form a torque-limiting or ratchet mechanism. When the adapter 132 is rotated, the teeth-like members 154 of the adapter 132 engage and ride up slightly on the corresponding pawl-like members 144 in order to rotate the collar 134. In turn, the collar 134 rotates the transmission member 135 to tighten the transmission member 135 to a mounting device or transmission component of a handpiece assembly.

The teeth-like members 154 of the adapter 132 and pawl-like members 144 of the collar 134 have a selected height. The teeth-like members 154 and/or pawl-like members 144 are preferably fabricated from a material having suitable resilient flexibility. As a result, the rotation of the adapter 132 will rotate the collar 134 until the transmission rod 135 is tightened against the mounting device at a desired and predetermined torque. After the transmission rod 135 is tightened to the desired torque, the teeth-like members 154 of the adapter 132 will slip on or pass over the pawl-like members 144 of the collar 134 as will be further described below.

In one embodiment, the pawl-like members 144 of the collar 134 are configured as ramps or wedges, and the teeth-like members 154 of the adapter 132 are configured as ribs or flanges. The teeth-like members 154 of the adapter 132 and the pawl-like members 144 of the collar 134 may be reversed so that the pawl-like members 144 of the collar 134 are ribs or flanges, and the teeth-like members 154 of the adapter 132 are ramps or wedges. It is also contemplated that the pawl-like members 144 may be integrally formed or coupled directly to the periphery of the transmission rod 136.

The angles of the faces of the teeth-like members 154 and the pawl-like members 144 and their height may also be varied to increase or decrease their frictional or gripping relationship to modify the slipping between the collar 134 and adapter 132, thereby changing the torque that may be applied when tightening the transmission rod 135 to the mounting device of the handpiece assembly. It is contemplated that the teeth-like members 154 and the pawl-like members 144 may be cooperating projections, wedges, cam surfaces, rachet-like teeth, serrations, wedges, flanges, or the like which cooperate to limit the torque applied to the transmission rod 135, without departing from the spirit and scope of the invention.

To attach the transmission rod 135 of the surgical instrument 120 to a handpiece assembly, the distal end of the mounting device or transmission component is threadedly connected to the proximal end of the transmission rod 135. The adapter 132 of the surgical instrument 120 is then manually rotated in a conventional screw-threading direction to interlock the threaded connection between the mounting device and the transmission rod 135. As the adapter 132 is rotated, the teeth-like members 154 of the adapter 132 engage the pawl-like members 144 of the collar 134 to turn the transmission rod 135.

When the transmission rod 135 is tightened to a predetermined torque on the mounting device, resistance increases and the pawl-like members 144 of the collar 134 start to overcome their frictional resistance on the teeth-like members 154 of the adapter 132. Particularly, the teeth-like members 154 of the adapter 132 cause the pawl-like members 144 of the collar 134 to resiliently flex or deflect from the applied force.

At a predetermined torque, the teeth-like members 154 of the adapter 132 slip past the pawl-like members 144 of the collar 134 into the adjacent notch or valley. Further rotation of the adapter 132 will cause circumferential ratcheting to occur between the teeth-like members 154 and the pawl-like members 144, permitting relative rotation between the adapter 132 and the collar 134. When this ratchet action occurs, adequate torque has been applied to the adapter 132 of the surgical instrument 120 to sufficiently tighten the transmission rod 135 to the mounting device of the handpiece assembly. Preferably, this occurs when the torque is within the range of from about 3 to about 20 inches/lbs., preferably 12 inches/lbs. It is also contemplated that the transmission member 135 may be tightened to the mounting device 135 to any suitable torque without departing from the spirit and scope of the invention.

The transmission rod 135 preferably has too small of a diameter to allow a user to apply excessive torque directly to the transmission rod 135. Therefore, it is difficult for a user to bypass or override the torque limiting device of the surgical tool 120.

To remove the surgical instrument 120 from the mounting device of the handpiece assembly, the adapter 132 is rotated in a conventional unthreading direction. When the adapter 132 is rotated, the teeth-like members 154 of the adapter 132 will catch or engage the sides of the pawl-like members 144 of the collar 134 to allow a relatively high disengaging torque to be applied to rotate the transmission rod 135 in the unthreading direction. As a result, the transmission rod 135 loosens from the mounting device. Once the transmission rod 135 is removed from the mounting device, the surgical instrument 120 may be thrown away or sterilized for reuse.

Figure 5:
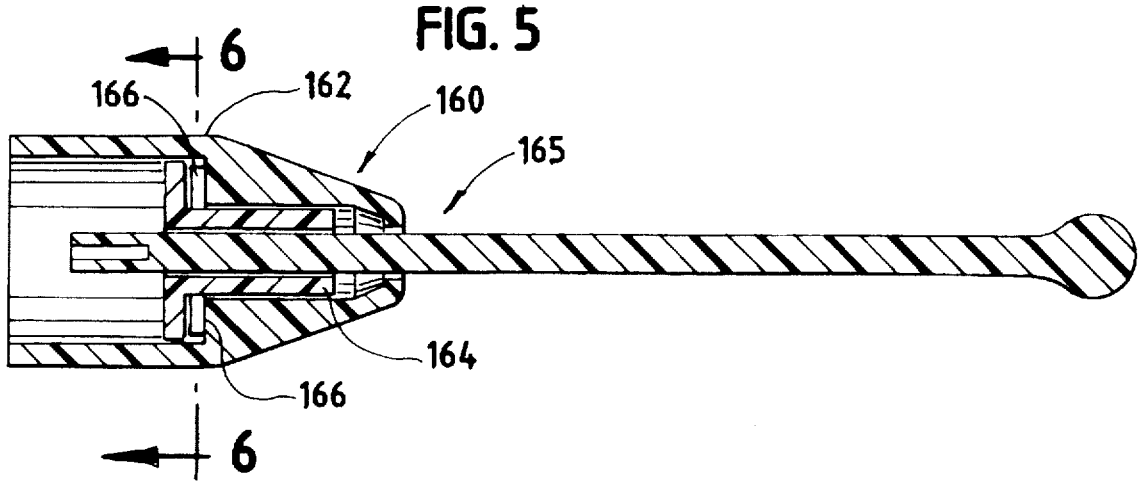
FIG. 5 is a cross-sectional view of another embodiment of a surgical instrument of the surgical system of FIG. 2.
Figure 6:
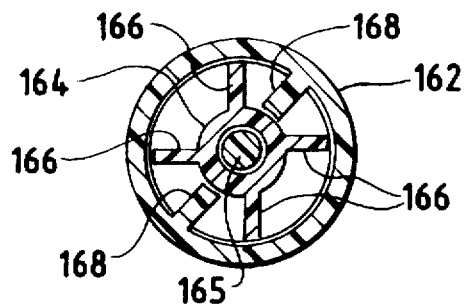
FIG. 6 is a cross-sectional view about line 6—6 of the surgical instrument of FIG. 5.
Figure 7:
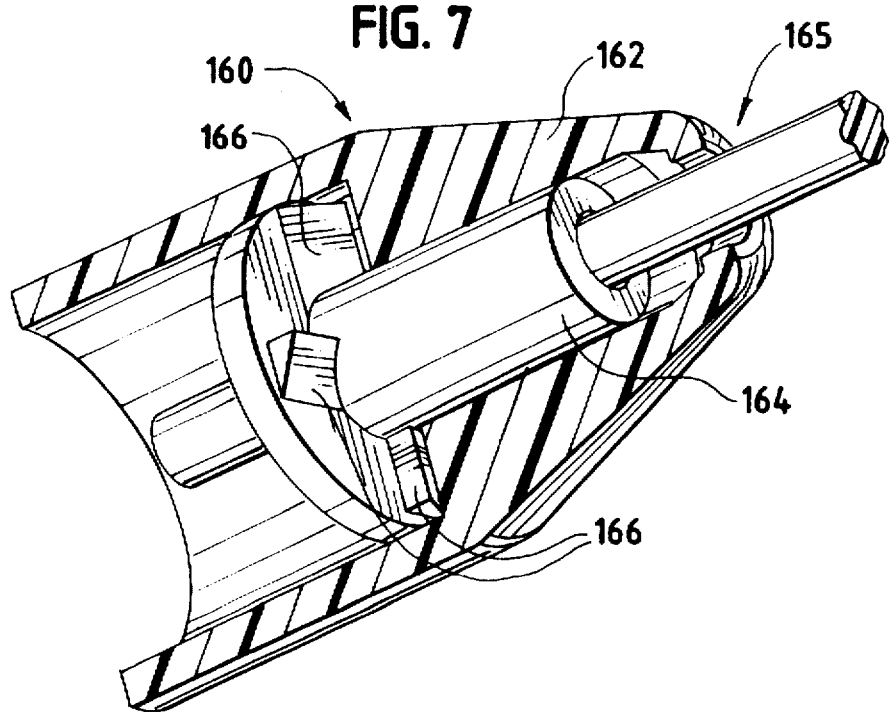
FIG. 7 is a cutaway view of a partial cross-section of the surgical instrument of FIG. 5.

Referring to FIGS. 5-7, another embodiment of a surgical instrument 160 is illustrated. The surgical instrument 160 includes an adapter or sleeve 162, a collar 164, and a working member 165, such as, for example, transmission rod integrally coupled to an end effector. The working member 165 may be attached and detached to a mounting device of a handpiece assembly in generally the same manner as discussed above. The working member 165 extends through an opening in the collar 164 and may be attached to the collar 164 near a node.

The collar 164 of the surgical instrument 160 is rotatably mounted within the adapter 162 and has one or more pawl-like or engageable members 166 as shown further in FIGS. 6-7. The collar 164 preferably has four pawl-like members 166 spaced about 360° at 90° intervals. Preferably, the pawl-like members 166 of the collar 164 are radially disposed on the collar 164 and have a height that extends parallel to the axis of the working member 165. It is contemplated that the collar 164 may have any suitable number of pawl-like members 166.

The adapter 162 of the surgical instrument 160 has one or more teeth-like or engaging members 168 that are configured to engage the pawl-like members 166 of the collar 164 to form a torque or rachet mechanism. As shown in FIG. 6, the adapter 162 preferably has two teeth-like members 168 spaced about 360° at 180° from each other. Preferably the teeth-like members 168 of the adapter 162 are radially disposed on the adapter 162 and have a height that extends parallel to the axis of the working member 165.

FIGS. 8 and 9 show an alternative embodiment of a surgical instrument 180 of a surgical system. The surgical instrument 180 preferably includes an adapter 182, an inner member 184, and a working member 186 or a transmission rod integrally attached to an end effector. The adapter 182 is preferably fabricated from a material having suitable resilience or flexibility to allow the inner member 184 to be rotated by the adapter 182 until a predetermined torque is reached.

The adapter 182 preferably has a bore 188 extending therethrough. The bore 88 has an inner surface having a selected geometric configuration, such as, for example, substantially polygonally or octagonally shaped (see FIG. 9), that substantially surrounds the inner member 184.

The inner member 184 has an outer surface that includes a complementary geometrical configuration that frictionally engages the inner surface of the bore 188 of the adapter 182. The inner member 184 is fabricated from a material having a suitable resilience to allow the adapter 182 to slip past the inner member 184 at a predetermined torque. The inner member 184 of the surgical instrument 180 is further coupled to the working member 186 so that when the inner member 184 rotates, the working member 186 also rotates. Preferably, the working member 186 extends through an opening in the inner member 184.

The inner member 184 of the surgical instrument 180 may rotate when the adapter 182 is turned in a conventional screw-threaded direction to tighten the working member 186 onto a mounting device or transmission component of a handpiece assembly. After the working member 186 is tightened to a desired or predetermined torque, the adapter 182 will continue to rotate without rotating the inner member 184. As a result, the inner member 184 and adapter 182 provide a torque limiting mechanism to prevent the working member 186 from being over-tightened to the mounting device of the handpiece assembly.

FIGS. 10 and 11 show an alternative embodiment of a surgical instrument 190 of a surgical system. The surgical instrument 190 preferably includes an adapter or sleeve 192, an inner member 194, and a working member 196, such as, for example, a transmission rod integrally attached to an end effector. The adapter 192 is preferably fabricated from a material having suitable resilience or flexibility to allow the inner member 194 to be rotated by the adapter 192 until a predetermined torque is reached.

The adapter 192 preferably has a bore 198 extending therethrough. The bore 198 has an inner surface having a selected geometric configuration, such as, for example, substantially cylindrically or elliptically shaped (see FIG. 11), that surrounds the inner member 194.

The inner member 194 has an outer surface that includes a complementary geometrical configuration that frictionally engages the inner surface of the bore 198 of the adapter 192. The inner member 194 is fabricated from a material having suitable resilience to allow the adapter 192 to slip past the inner member 194 at a predetermined torque. The inner member 194 is preferably coupled to the working member 196 so that when the inner member 194 rotates, the working member 196 also rotates. Preferably, the working member 196 extends through an opening of the inner member 194.

The inner member 194 of the surgical instrument 180 may rotate when the adapter 192 is turned in a conventional screw-threaded direction to tighten the working member 196 onto a mounting device of a handpiece assembly. After the working member 196 is tightened to a desired or predetermined torque, the adapter 192 will continue to rotate without rotating the inner member 194. Hence, the inner member 194 and adapter 192 provide a torque limiting mechanism to prevent the working member 196 from being over tightened to the mounting device of the handpiece assembly.

Figure 12:
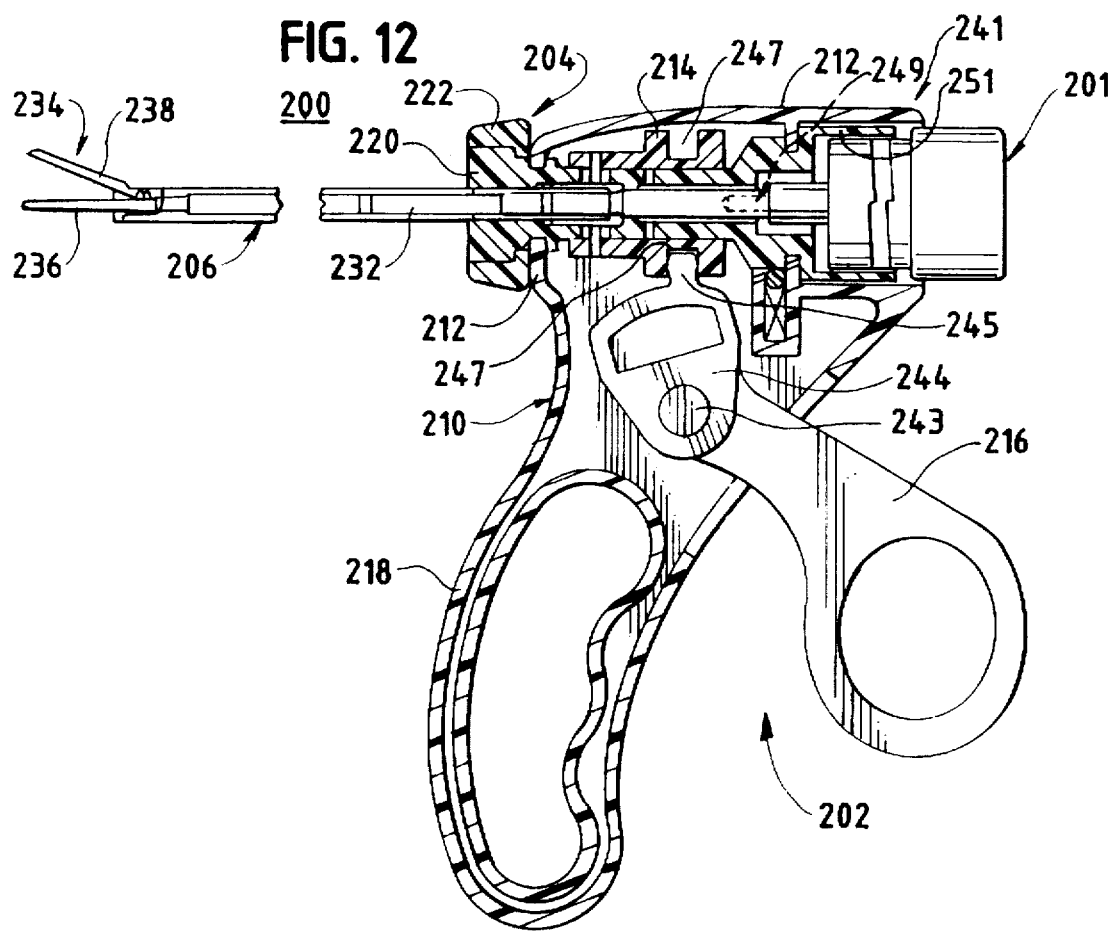
FIG. 12 is a fragmentary partial cross-sectional view of an embodiment of an ultrasonic transector in accordance with the present invention.

Referring now to FIG. 12, a preferred embodiment of an ultrasonic transector 200 is illustrated. The transector 200 generally includes a handpiece assembly 201, a scissors grip portion 202, a ratchet assembly 204, a sheath 206, a transmission rod or waveguide 232, an actuator rod, and a clamping assembly 234. The handpiece assembly 201 is substantially similar to the handpiece assembly 50 described above. As such, further description of the handpiece assembly 201 is unnecessary for a complete understanding of the present invention.

In one embodiment, the proximal end of the transmission rod 232 is screw threaded onto a stud 249 projecting from the handpiece assembly 201. The transmission rod 232 extends through the sheath 206 of the transector 200 and is coupled to the clamping assembly 234. The transmission rod 232 may have a diameter of, for example, about 0.3 mm. It is contemplated that the transmission rod 232 may be any suitable diameter. The transmission rod 232 may also be fabricated from any suitable material as described above.

The clamping assembly 234 of the transector 200 generally includes an active end or blade 236 and a non-vibrating upper jaw portion 238 for gripping tissue, compressing tissue, or the like. The clamping assembly 234 is illustrated in FIG. 12 in a clamp open position and is preferably pivotally attached to the actuator rod of the transector 200. The upper jaw portion 238 is pivotally carried in a recess on the distal end of the transmission rod 232. Ultrasonic vibrations are transmitted along the transmission rod 232 in a longitudinal direction to vibrate the active end 236 of the clamping assembly 234. The active end 236 is preferably nonrotatable.

The scissors grip portion 202 of the transector 200 generally includes a housing 212, a handle 210, a nose cone or adapter 241, and an inner mechanism 214. The inner mechanism 214 is disposed in the housing 212 for movement about a longitudinal axis of the transmission rod 232 and may be rotatable about that axis. The inner mechanism 214 is preferably coupled or attached to the transmission rod 232 to translate rotation motion of the scissors grip portion 202 to linear motion of the actuator rod.

The nose cone 241 of the scissors grip portion 202 preferably includes an internally cup-shaped housing 251.

The cup-shaped housing 251 allows the distal end of the handpiece assembly 201 to slide into the housing 251 in order to support the transector 200 on the distal end of the handpiece assembly 201.

The handle 210 of the scissors grip portion 202 includes a finger handle or grip 218 and a thumb handle or trigger arm 216 pivotally mounted to the housing 212 by a pin 243. The trigger arm 216 is also fixed to a link 244 having a projection knob 245. The projection knob 245 is positioned in an annular recess or groove 247 along the lower side of the inner mechanism 214 of the scissors grip portion 202.

When the trigger arm 216 is moved toward the finger grip 218, the link 244 slides inner mechanism 214 toward the handpiece assembly 201. The movement of the inner mechanism 214 toward the handpiece assembly 201 displaces the actuator rod rearwardly to pivot the clamping assembly 234 into its closed position. The movement of the trigger arm 216 in the opposite direction slides the inner mechanism 214 to displace the actuator rod in the opposite direction, i.e., forwardly, and hence pivot the clamping assembly 234 into its open position.

Figure 13:
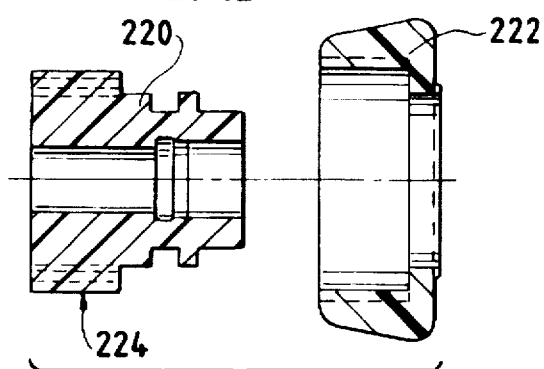
FIG. 13 is an exploded cross-sectional view of a ratchet assembly of the ultrasonic transector of FIG. 12.
Figure 14:
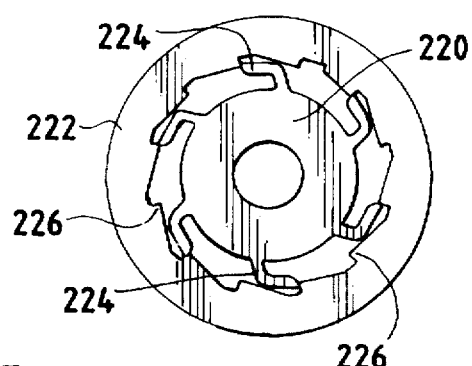
FIG. 14 is an end view of one embodiment of the ratchet assembly of FIG. 13.
Figure 15:
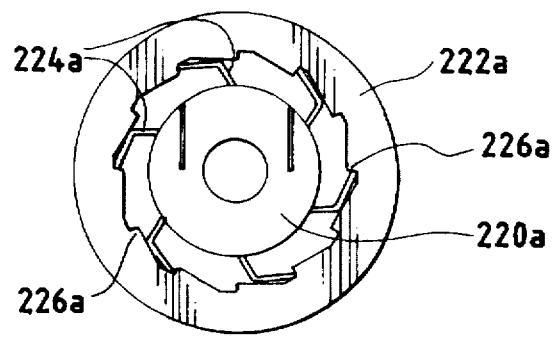
FIG. 15 is an end view of an alternative embodiment of the ratchet assembly of FIG. 13.

Referring still to FIG. 12, the ratchet assembly 204 of the transector 200 is rotatably coupled to the housing 212 of the scissors grip portion 202. The ratchet assembly 204 includes an inner ratchet 220 and an outer ratchet 222 as further shown in FIGS. 13-15. The inner ratchet 220 is preferably fixedly attached to the sheath and includes ratchet arms 224 that engage with the saw tooth ramps 226 of the outer ratchet 222. It is contemplated that the inner ratchet 220 and the outer ratchet 222 may be constructed from any suitable material without departing from the spirit and scope of the invention. The inner ratchet 220 may be a one-piece plastic construction as shown in FIG. 14 or the inner ratchet 220a may have a plastic hub 220a with metallic ratchet arms 224a to engage the saw tooth ramps 226a of the outer ratchet 222a as illustrated in FIG. 15. The ratchet arms 224 and ramps 226 may be any suitable shape as those skilled in the art will recognize.

When the outer ratchet 222 is rotated in a screw-threaded direction the outer ratchet 222 causes the ratchet arms 224 of the inner ratchet 220 to deflect as they move up on the ramps 226 of the outer ratchet 222. As a result, torque is transmitted from the outer ratchet 222 to the inner ratchet 220 by the deflection of the ratchet arms 224 of inner ratchet 220 on the ramps 226 of the outer ratchet 222. The deflection of the ratchet arms 224 increases the contact and friction force between the ratchet arms 224 and the ramps 226 until the ratchet arms 224 of the inner ratchet 220 ride over the peaks of the ramps 226 of the outer rachet 222 into the next valley at a predetermined torque. When the outer ratchet 222 is rotated in an unthreading direction, the ratchet arms 224 of the inner ratchet 220 catch the sides of the ramps 226 of the outer ratchet 222 to allow high removal torque to be transmitted. It is also contemplated that the inner ratchet 220 may have ramps and the outer ratchet 222 may have ratchet arms.

Figure 16:
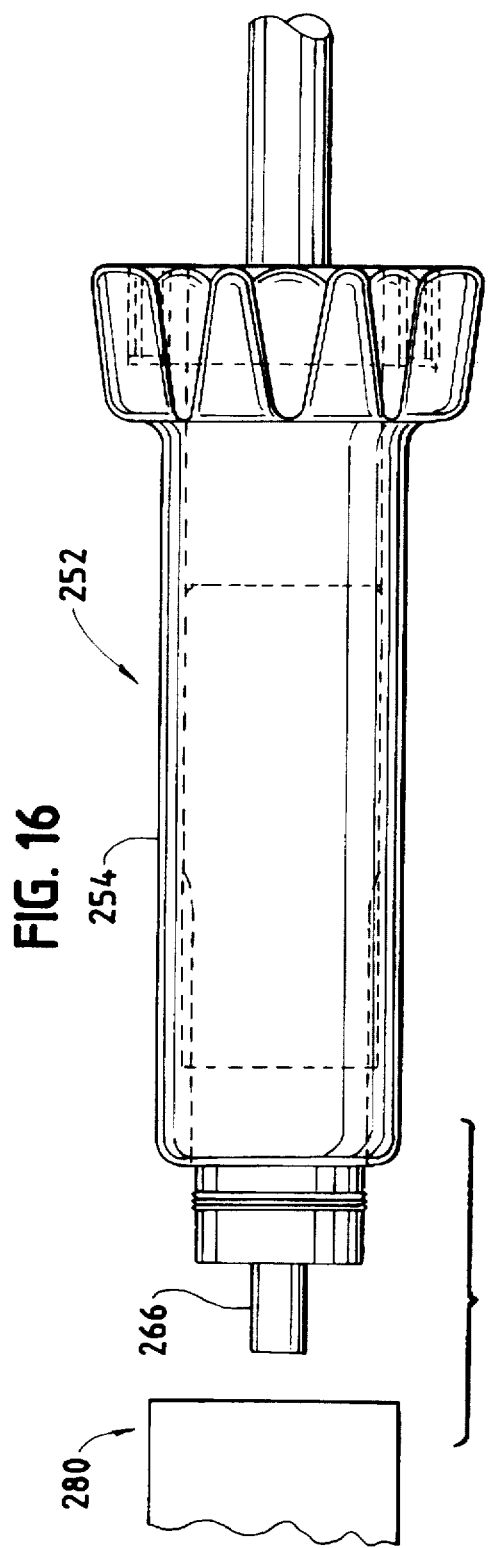
FIG. 16 is a side view of another embodiment of a handpiece assembly in accordance with the present invention.
Figure 17:
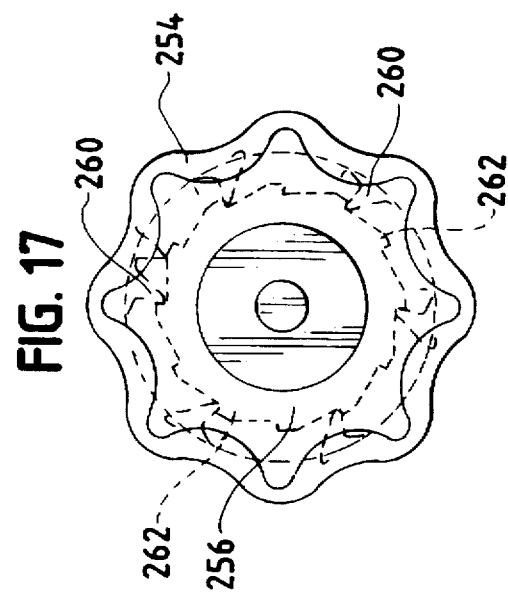
FIG. 17 is an end view of a rachet assembly of the handpiece assembly of FIG. 16.

Referring now to FIGS. 16–17, another preferred embodiment of a handpiece assembly 252 is illustrated. The handpiece assembly 252 preferably provides a torque limiting mechanism to limit the amount of torque applied when attaching a mounting device 266 to a transmission component or rod of a surgical instrument 280.

The handpiece assembly 252 is substantially similar to the handpiece assembly 50 described above except that the housing assembly 250 preferably includes an outer rotatable sleeve or outer ratchet member 254 disposed over the housing 256 as shown in FIG. 16. The housing 256 preferably includes one or more ramps 262 extending outwardly in a radial direction, as shown in FIG. 17.

The sleeve 254 of the handpiece assembly 252 includes arms 260 to engage the ramps 262 of the housing 256. The housing 256 and sleeve 254 provide a rachet mechanism to limit the amount of torque when the transmission rod of the surgical instrument 280 is tightened to the mounting device 266 of the handpiece assembly 252. It is also contemplated that the torque may be limited by any suitable means, such as slip clutches, axial arrangements, radial arrangement, and the like, without departing from the spirit and scope of the invention. The sleeve 254 preferably prevents the user from gripping the inner housing 256 so that excess torque can not be applied.

When the sleeve 254 is rotated in a conventional screw-threaded direction the arms 260 of the sleeve 254 engage the ramps 262 of the housing 256. As a result, torque is transmitted from the sleeve 254 to the housing 256 by the deflection of the ramps 262 of the housing 256 on the arms 260 of the sleeve 254. The deflection of the arms 260 increases the contact and friction force between the arms 260 and the ramps 262 until the arms 260 of the sleeve 254 ride over the peaks of the ramps 262 of the housing 256 into the next valley at a predetermined torque. When the sleeve 254 is rotated in an unthreading direction, the ramps 262 of the housing 256 catch or engage the sides of the arms 260 of the sleeve 254 to allow high removal torque to be transmitted.

The methods and devices of the present invention allow a transmission component of a surgical instrument to be tightened to a transmission component, such as a mounting device, of a handpiece assembly to predetermined torque without the use of a separate instrument. The transmission component of the surgical instrument may be easily attached or removed from the handpiece assembly allowing for a variety of transmission components to be quickly attached to the mounting device of the handpiece assembly during an operation. An integral torque mechanism prevents the transmission component of the surgical instrument from being over-tightened to the mounting device of the handpiece assembly. The integral torque mechanism may be incorporated in the handpiece assembly or the surgical instrument.

Although the present invention has been described in detail by way of illustration and example, it should be understood that a wide range of changes and modifications can be made to the preferred embodiments described above without departing in any way from the scope and spirit of the invention. Thus, the described embodiments are to be considered in all aspects only as illustrative and not restrictive, and the scope of the invention is, therefore, indicated by the appended claims rather than the foregoing description. All changes that come within the meaning and range of equivalency of the claims are to be embraced within their scope.

What is claimed is:

1. An ultrasonic surgical instrument comprising:
   a working member having a first end and a second end, the working member adapted to receive ultrasonic vibration and to transmit the ultrasonic vibration from the first end to the second end of the working member;
   a collar coupled to the working member, the collar having at least one tooth like member;
   an adapter having at least one pawl-like member wherein the at least one pawl-like member of the adapter is engageable with the at least one tooth-like member of the collar so that the collar can rotate with the rotation of the adapter and the at least one pawl-like member of the adapter to slip out of engagement with the at least one tooth-like member of the collar when a predetermined torque is applied.

2. The device of claim 1 wherein the height of the at least one pawl-like member and at least one tooth-like member extends substantially parallel to the axis of the working member.

3. The device of claim 1 wherein the height of the at least one pawl-like member and at least one tooth-like member extends in a substantial radial direction.

4. The device of claim 1 wherein the adapter includes a plurality of pawl-like members.

5. The device of claim 1 wherein the collar includes a plurality of tooth-like members.

6. The device of claim 1 wherein the working member comprises a transmission rod and an end effector.

7. The device of claim 1 wherein the at least one tooth-like member is disposed on the outer periphery of the collar and the at least one pawl-like member is disposed on the inner surface of the adapter.

8. A surgical device comprising:
   a transducer adapted to vibrate at an ultrasonic frequency in response to electrical energy;
   a housing carrying the transducer, the housing having an outer surface;
   a tooth-like member disposed on the outer surface of the housing;
   a sleeve disposed around the housing, the sleeve having an inner surface;
   a pawl-like member disposed on the inner surface of the sleeve to engage the tooth-like member of the housing so that the sleeve can rotate with the housing until the pawl-like member of the sleeve slips out of engagement with the tooth-like member of the housing when a predetermined torque is applied.

9. A surgical instrument comprising:
   a working member adapted to contact tissue of a patient;
   a collar coupled to the working member, the collar having teeth means; and
   an adapter having pawl means engageable with the teeth menas of the collar so that the collar will rotate with the rotation of the adapter until the pawl means of the adapter slips past the teeth means of the collar when a predetermined torque is applied.

10. The device of claim 9 wherein the height of the teeth means and pawl means extends substantially parallel to the axis of the working member.

11. The device of claim 9 wherein the height of the teeth means and pawl means extends substantially perpendicular to the axis of the working member.

* * * * *